(12) United States Patent
Mixson

(10) Patent No.: US 7,465,708 B2
(45) Date of Patent: *Dec. 16, 2008

(54) BRANCHED CATIONIC COPOLYMERS AND METHODS FOR ANTIMICROBIAL USE

(76) Inventor: A. James Mixson, 15620 Thistlebridge Dr., Rockville, MD (US) 20853

( * ) Notice: Subject to any disclaimer, the term of this patent is extended or adjusted under 35 U.S.C. 154(b) by 345 days.

This patent is subject to a terminal disclaimer.

(21) Appl. No.: 10/535,991

(22) PCT Filed: Nov. 25, 2003

(86) PCT No.: PCT/US03/37467

§ 371 (c)(1),
(2), (4) Date: May 25, 2005

(87) PCT Pub. No.: WO2004/048421

PCT Pub. Date: Jun. 10, 2004

(65) Prior Publication Data

US 2006/0281683 A1    Dec. 14, 2006

Related U.S. Application Data

(60) Provisional application No. 60/428,825, filed on Nov. 25, 2002.

(51) Int. Cl.
*A61K 38/10* (2006.01)
(52) U.S. Cl. .................................. 514/14; 530/329
(58) Field of Classification Search .................. None
See application file for complete search history.

(56) References Cited

U.S. PATENT DOCUMENTS

| | | | |
|---|---|---|---|
| 4,847,240 A | 7/1989 | Ryser et al. | |
| 5,354,844 A | 10/1994 | Beug et al. | |
| 5,554,388 A | 9/1996 | Illum et al. | |
| 5,670,347 A | 9/1997 | Gopal | |
| 5,736,392 A | 4/1998 | Hawley-Nelson et al. | |
| 5,856,435 A | 1/1999 | Bazile et al. | |
| 5,912,230 A * | 6/1999 | Oppenheim et al. | 514/12 |
| 5,985,354 A | 11/1999 | Mathiowitz et al. | |
| 6,051,429 A | 4/2000 | Hawley-Nelson et al. | |
| 6,113,946 A | 9/2000 | Szoka, Jr. et al. | |
| 6,312,727 B1 | 11/2001 | Schacht et al. | |
| 6,372,499 B1 | 4/2002 | Midoux et al. | |
| 6,475,004 B2 | 11/2002 | Shuey et al. | |
| 6,692,911 B2 | 2/2004 | Pack et al. | |
| 7,070,807 B2 * | 7/2006 | Mixson | 424/484 |
| 7,163,695 B2 * | 1/2007 | Mixson | 424/486 |
| 2001/0006817 A1 | 7/2001 | Pack et al. | |

FOREIGN PATENT DOCUMENTS

| | | |
|---|---|---|
| EP | 0 727 223 A1 | 8/1996 |
| WO | WO-98/22610 A1 | 5/1998 |
| WO | WO-99/42091 A1 | 8/1999 |
| WO | WO-00/32764 A1 | 6/2000 |
| WO | WO-01/47496 A1 | 7/2001 |

OTHER PUBLICATIONS

Midoux et al., Membrane Permeabilization and Efficient Gene Transfer by a Peptide Containing Several Histidines. *Bioconjugate Chem* 98, 9, 260-267.

Midoux et al., Efficient Gene Transfer by Histidylated Polylysine/pDNA Complexes. *Bioconjugate Chem* May-Jun. 1999; 10(3):406-411.

Chen et al., Co-polymer of histidine and lysine markedly enhances transfection efficiency of liposomes. *Gene Ther* Oct. 2000; 7(19):1698-1705.

Chen et al., Branched co-polymers of histidine and lysine are efficient carriers of plasmids. *Nucleic Acids Res* Mar. 15, 2001; 29(6):1334-1340.

Pichon et al., Histidylated oligolysines increase the transmembrane passage and the biological activity of antisense oligonucleotides. *Nucleic Acids Res* Jan. 15, 2000; 28(2):504-512.

Putnam, D. et al., Polymer-based gene delivery with low cytotoxicity by a unique balance of side-chain termini. *PNAS* 98(3), Jan. 30, 2001, pp. 1200-1205.

Bechinger, B., Kinder, R., Helmle, M., Voogt, T.C., Harzer, U. and Schinzel, S. (1999). Peptide structural analysis by solid-state NMR spectroscopy. *Biopolymers* 51, 174-90.

Bellm, L., Lehrer, R. J. and Ganz, T. (2000). Protegrins: new antibiotics of mammalian origin. *Expert Opin Investig Drugs* 9, 1731-42.

Blanc, E., Fremont, V., Sizun, P., Meunier, S., Van Rietschoten, J., Thevand, A., Bernassau, J.M. and Darbon, H. (1996). Solution structure of PO1, a natural scorpion peptide structurally analogous to scorpion toxins specific for apamin- sensitive potassium channel. *Proteins* 24, 359-69.

Bontems, F., Roumestand, C., Gilquin, B., Menez, A. and Toma, F. (1991). Refined structure of charybdotoxin: common motifs in scorpion toxins and insect defensins. *Science* 254, 1521-3.

Chen, Q.R., Zhang, L., Stass, S.A. and Mixson, A.J. (2001). Branched co-polymers of histidine and lysine are efficient carriers of plasmids. *Nucleic Acids Res.* 29, 1334-1340.

Cruz, L.J., Johnson, D.S. and Olivera, B.M. (1987). Characterization of the omega-conotoxin target. Evidence for tissue-specific heterogeneity in calcium channel types. *Biochemistry* 26, 820-4.

(Continued)

*Primary Examiner*—Christopher R. Tate
*Assistant Examiner*—Roy Teller
(74) *Attorney, Agent, or Firm*—Connolly Bove Lodge & Hutz LLP

(57) ABSTRACT

The invention provides a branched copolymer for the treatment of bacterial, fungal, and viral infections. The branched copolymer is characterized as having (i) at least 10 amino acids, (ii) at least 10% of the amino acids are histidine, (iii) at least 10% of the amino acids are non-histidine, (iv) said branched polymer comprising one or more backbones, (v) one or more terminal branches, and (vi) optionally, one or more non-terminal branches.

15 Claims, 1 Drawing Sheet

OTHER PUBLICATIONS

Figure 1:
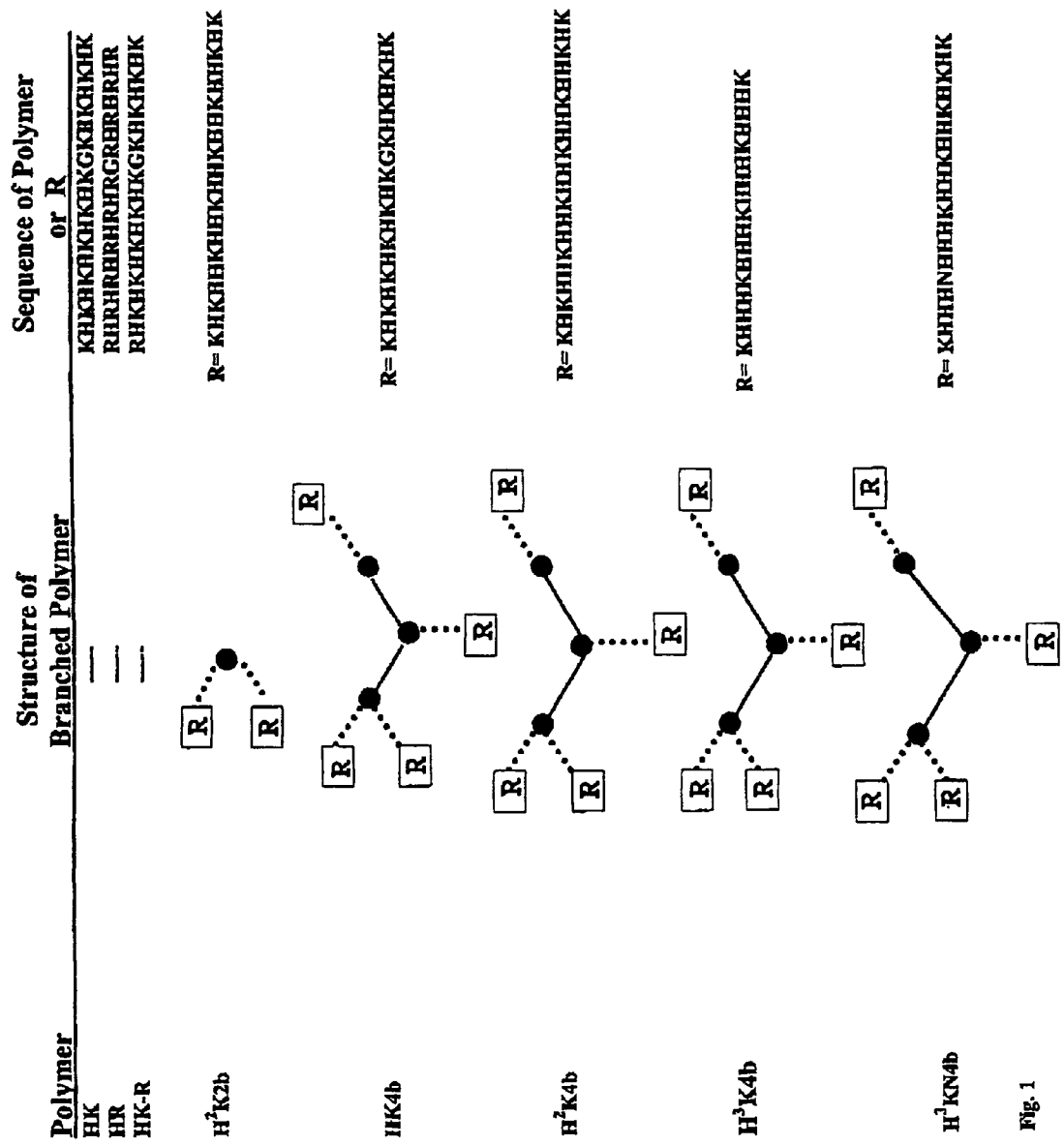

Dathe, M. and Wieprecht, T. (1999). Structural features of helical antimicrobial peptides: their potential to modulate activity on model membranes and biological cells. *Biochim Biophys Acta* 1462, 71-87.

Epand, R.M. and Vogel, H.J. (1999). Diversity of antimicrobial peptides and their mechanisms of action. *Biochim Biophys Acta* 1462, 11-28.

Giacometti, A., Cirioni, O., Ghiselli, R., Viticchi, C., Mocchegiani, F., Riva, A., Seba, V. and Scalise, G. (2001). Effect of mono-dose intraperitoneal cecropins in experimental septic shock. *Crit Care Med* 29, 1666-9.

Gilles, M., Krimm, J., Bouet, F., Froy, O., Gurevitz, M., Lancelin, J.M. and Gordon, D. (2000). Structural implications on the interaction of scorpion alpha-like toxins with the sodium channel receptor site inferred from toxin iodination and pH-dependent binding. *J Neurochem* 75, 1735-45.

Hancock, R.E. (1997). Peptide antibiotics. *Lancet* 349, 418-22.

Hancock, R.E. (1999). Host defense (cationic) peptides: what is their future clinical potential? *Drugs* 57, 469-73.

Hancock, R.E. and Lehrer, R. (1998). Cationic peptides: a new source of antibiotics. *Trends Biotechno* 16, 82-8.

Harder, J., Bartels, J., Christophers, E. and Schroder, J.M. (2001). Isolation and characterization of human beta-defensin-3, a novel human inducible peptide antibiotic. *J Biol Chem* 276, 5707-13.

Hoover, D.M., Chertov, O. and Lubkokwski, J. (2001). The structure of human beta-defensin-1: new insights into structural properties of beta-defensins. *J Biol Chem* 276, 39021-6.

Hughes, A.L. (1999). Evolutionary diversification of the mammalian defensins. *Cell Mol Life Sci* 56, 94-103.

Jia, H.P., Mllls, J.N., Barahmand-Pour, F., Nishimura, D., Mallampali, R.K., Wang G., Wiles, K., Tack, B.F., Bevins, C.L. and McCray, P.B., Jr. (1999). Molecular cloning and characterization of rat genes encoding homologues of human beta-defensins. *Infect Immun* 67, 4827-33.

Kourie, J.I. and Shorthouse, A.A. (2000). Properties of cytotoxic peptide-formed ion channels. *Am J Physiol Cell Physiol* 278, C1063-87.

La Rocca, P., Biggin, P.C., Tieleman, D.P. and Sansom, M.S. (1999). Simulation studies of the interaction of antimicrobial peptides and lipid bilayers. *Biochim Biophys Acta* 1462, 185-200.

Lehrer, R.I. and Ganz, T. (1996). Endogenous vertebrate antibiotics. Defensins, protegrins, and other cysteine-rich antimicrobial peptides. *Ann NY Acad Sci* 797, 228-39.

Mallow, E.B., Harris, A., Salzman, N., Russell, J.P., DeBerardinis, R.J., Ruchelli, E. and Bevins, C.L. (1996). Human enteric defensins. Gene structure and developmental expression. *J Biol Chem* 271, 4038-45.

Martin, M.F. and Rochat, H. (1984). Purification of thirteen toxins active on mice from the venom of the North African scorpion *Buthus occitanus tunetanus*. *Toxicon* 22, 279-91.

Mosca, D.A., Hurst, M.A., So, W., Viajar, B.S., Fujii, C.A. and Falla, T.J. (2000). IB-367, a protegrin peptide with in vitro and in vivo activities against the microflora associated with oral mucositis. *Antimicrob Agents Chemother* 44, 1803-8.

Oppenheim, F.G., Xu, T., McMillian, F.M., Levitz, S.M., Diamond, R.D., Offner, G.D. and Troxler, R.F. (1988b). Histatins, a novel family of histidine-rich proteins in human parotid secretion. Isolation, characterization, primary structure, and fungistatic effects on *Candida albicans*. *J Biol Chem* 263, 7472-7.

Oppenheim, F.G., Xu, T., McMillian, F.M., Levitz, S.M., Diamond, R.D., Offner, G.D. and Troxler, R.F. (1988a). Histatins, a novel family of histidine-rich proteins in human parotid secretion. Isolation, characterization, primary structure, and fungistatic effects on *Candida albicans*. *J Biol Chem* 263, 7472-7.

Oren, Z., Lerman, J.C., Gudmundsson, G.H., Agerberth, B. and Shai, Y. (1999). Structure and organization of the human antimicrobial peptide LL-37 in phospholipid membranes: relevance to the molecular basis for its non-cell-selective activity. *Biochem J* 341, 501-13.

Oren, Z. and Shai, Y. (1998). Mode of action of linear amphipathic alpha-helical antimicrobial peptides. *Biopolymers* 47, 451-63.

Oren, Z., Ramesh, J., Avrahami, D., Suryaprakash, N., Shai, Y. and Jelinek, R. (2002), Structures and mode of membrane interaction of a short alpha helical lytic peptide and its diastereomer determined by NMR, FTIR, and fluorescence spectroscopy, *Eur J Biochem* 269, 3869-80.

Otvos, L, Jr. (2000). Antibacterial peptides isolated from insects. *J Pept Sci* 6, 497-511.

Otvos, L., Jr., Bokonyi, K., Varga, L, Otvos, B.I., Hoffmann, R., Ertl, H.C., Wade, J.D., McManus, A.M., Craik, D.J. and Bulet, P. (2000). Insect peptides with improved protease-resistance protect mice against bacterial infection. *Protein Sci* 9, 742-9.

Peschel, A. and Collins, L.V. (2001). Staphylococcal resistance to antimicrobial peptides of mammalian and bacterial origin. *Peptides* 22, 1651-9.

Sabatini, L.M. and Azen, E.A. (1989). Histatins, a family of salivary histidine-rich proteins, are encoded by at least two loci (HIS1 and HIS2). *Biochem Biophys Res Commun* 160, 495-502.

Sitaram, N. and Nagaraj, R. (1999). Interaction of antimicrobial peptides with biological and model membranes: structural and charge requirements for activity. *Biochim Biophys Acta* 1462, 29-54.

Thomas, N.J., Carcillo, J.A., Doughty, L.A., Sasser, H. and Heine, R.P. (2002). Plasma concentrations of defensins and lactoferrin in children with severe sepsis. *Pediatr Infect Dis J* 21, 34-8.

Tsai, H. and Bobek, L.A. (1998). Human salivary histatins: promising anti-fungal therapeutic agents. *Crit Rev Oral Biol Med* 9, 480-97.

Vogel, H.J., Schibli, D.J., Jing, W., Lohmeier-Vogel, E.M., Expand, R.F. and Expand, R.M. (2002). Towards a structure function analysis of bovine lactoferricin and related tryptophan- and arginine-containing peptides, *Biochem Cell Biol* 80, 49-63.

Yang, D., Biragyn, A., Kwak, L.W. and Oppenheim, J.J. (2002). Mammalian defensins in immunity: more than just microbicidal. *Trends Immunol* 23, 291-6.

\* cited by examiner

BRANCHED CATIONIC COPOLYMERS AND METHODS FOR ANTIMICROBIAL USE

REFERENCE TO RELATED APPLICATION

This is a National Stage application under 35 U.S.C. § 371 of PCT/US2003/037467 (WO2004/048421), filed Nov. 25, 2003, which claims priority of 60/428,825, filed 25 Nov. 2002.

FEDERAL SPONSORSHIP

The U.S. Government has a paid-up license in this invention and the right in limited circumstances to require the patent owner to license others on reasonable terms as provided for by the terms of Grant Number 5R29CA70394-05 awarded by the National Institutes of Health, National Cancer Institute.

1. BACKGROUND OF THE INVENTION

1.1 Field of Invention

The present invention relates generally to antimicrobial agents, more particularly to antimicrobial peptides, and most specifically to branched cationic antimicrobial peptides.

1.2 General Background

Increasing bacterial resistance to conventional antibiotics has spurred research for novel antimicrobial agents. One such area concerns antimicrobial peptides (Hancock, 1999; Hancock and Lehrer, 1998, Lehrer and Ganz, 1996). Cationic peptides have an important role in defending the host against invading microbial organisms in both plants and animals (Otvos, 2000; Otvos et al., 2000). The activity of some cationic peptides are restricted to either gram positive or gram negative bacteria while others are active against both. Cationic peptides are also effective against fungal and viral infection Hancock, 1999).

Cationic peptides are small, 12-35 amino acids, diverse both in sequence and structure, and often possess a net positive charge due to the presence of arginine and lysine (Hancock, 1999). Since living organisms lack the ability to synthesize branched peptides all cationic microbial peptides are linear and this limits antimicrobial activity. Four major classes of antimicrobial peptides by structure are recognized: β-stranded, e.g. defensins and protegrins; α-helical, e.g. magainins and cecropins; extended coil, e.g. indolicidin and bac 5; and loops, e.g. bacteninin and polymyxins (Hancock, 1997).

1.3 Discussion of Prior Art

Patent literature has described microbial activity by several cationic peptides: WO 8900199; WO 885826, WO 8604356, EP 193351, EP 85250, U.S. Pat. Nos. 6,465,429, & 5,912,230. Helicity, hydrophobicity, and charge are considered important to cationic peptide selectivity toward prokaryotic membranes (Dathe and Wieprecht, 1999; Hoover et al., 2001; Hughes, 1999).

In addition to cationic amino acids cysteine, proline, glycine, histidine, and hydrophobic amino acids appear to have a structural functional role in selected microbial peptides (Ibid., Epand and Vogel, 1999; La Rocca et al., 1999; Oppenheim et al., 1998a; Sitaram and Nagaraj, 1999). Histidine, for example, is not present in many antimicrobial peptides but is found in the saliva in one group of low molecular weight linear peptides: Histatin 1 and 3 (Oppenheim et al., 1998b; Sabatini and Azen, 1989; Tsai and Bobek, 1998). Proteolytic fragments of Histatin 1 and 3 have been shown to have antifungal activity (Ibid.).

Defensins and protegrins are the primary antimicrobial peptides in humans wherein the former is abundant in phagocytes and small intestinal mucosa. Increases in serum defensins in non-neutropenic patients with sepsis have been observed and it has been suggested that defensins play a role in host defense against severe sepsis (Thomas et al., 2002). The role antimicrobial peptides have in host protection against systemic infections is not clear but the role played in prevention and control of local infections, particularly in higher organisms, is well evidenced.

Prokaryotes have several properties heightening sensitivity to cationic microbial peptides in comparison with eukaryotes. The almost universal negative charge on cell membranes and walls of bacteria is considered responsible for the antibacterial activity of cationic peptides. This charge is partly due to certain components: lipopolysaccharide (LPS) and anionic lipids in membranes; peptidoglycans and techoic acid in walls. Eukaryotic cell walls, in contrast, lack anionic lipids. A lack of cholesterol and lesser potential for membrane transfer also increase the sensitivity of prokaryote bacteria in comparison with eukaryotes and the combination of these properties enable cationic peptides to target and klll the former. At high concentrations, however, cationic peptides may be toxic to eukaryotic cells.

Gram negative bacteria have a peptidoglycan layer between the inner and outer cell membranes. Cationic peptides first bind to the negatively charged LPS in the outer membrane and then bind to the anionic lipids of the inner membrane in a self promoting mechanism. Both actions require a positive charge and this also enables penetration of the single inner membrane of gram positive bacteria. A sufficient number of cationic amino acids with a positive charge at physiologic pH is clearly necessary. Two mechanisms have been suggested for this: formation of a trans-membrane pore; and membrane solubilization. The latter appears to be the primary mechanism for inhibiting prokaryotic bacterial growth (Bechinger et al., 1999; Oren et al., 1999; Oren eta al., 2002; Oren and Shai, 1998) while the provision of a cationic cleavage peptide by lactoferrin (Vogel et al., 2002) supports the former. It has been suggested, moreover, that these mechanisms are not mutually exclusive and that not all antimicrobial peptides act by the same mechanism (Ibid.) In addition to these prokaryotic membrane destruction mechanisms β-defensins may enhance host defenses by reducing endotoxin levels (Giacometti et al., 2001) or by interacting with chemokine receptors (Yang et al., 2002).

Some bacteria evidently have outer membranes that are impenetrable by cationic peptides (Hancock, 1997; Preschel and Collins, 2001) and while synergism between several different type of antibiotics and cationic peptides has been shown in pre-clinical models (Hancock, 1999) and IB-367 has been evaluated in phase II clinical trials on oral mucositis (Bellm et al., 2000; Mosca et al., 2000) little is known about acute or chronic toxicity of may cationic peptides administered intravenously.

Defensins are similar to neurotoxic venoms in being small cationic peptides with cysteine bridges (Bontems et al., 1991; Kourie and Shorthouse, 2000) but are dissimilar in not affecting ion channel activity. Many defensins (Harder et al., 2001; Jia et al., 1999; Mallow et al., 1996) and neurotoxins (Blanc et al., 1996; Cruz et al., 1987; Gilles et al., 2000; Martin and Rochat, 1984) have histidines in close proximity with cationic amino acids and since the role of histidines in neurotoxins has not been investigated this similarity urges caution in development of cationic peptides de novo.

Non-viral gene therapy carriers are also cationic, often contain arginine and lysine, and the resulting positive charge is important to both interaction with DNA and the cell surface. Branched polymers have been made primarily from histidine and lysines (Chen et al., 2001, WO 147496) that, in contrast to cationic liposomes, are effective carriers of DNA into cells. The role of histidine in these non-viral gene therapy carriers is thought to be the buffering of endosomes but endosomes have no role in the antimicrobial activity of cationic peptides.

1.4 Statement of Need

The similarity of defensins to neurotoxins in being linear small cationic peptides with cysteine bridges has been noted as urging caution in the development of cationic peptides de novo for use as an antibiotic. Toxicity to cardiac and neural cells is recognized as a grave concern particularly for a systemic antibiotic for both natural and de novo peptides.

While the prior art has, as related above, demonstrated widespread success of defensins possessing cationic amino acids in fighting local infections in vivo and of cationic peptides as an antimicrobial in vitro, the development of an effective antimicrobial peptide with minimal toxicity is essential.

The demonstrated ability of bacteria in recent years to develop resistance to all known antibiotics, including, most recently and most alarmingly, strains resistant to vancomycin, the antibiotic of last resort, is a problem of vast dimension. Bacterial infection has, again, become a primary concern of surgical medicine. And while for obvious reasons the phenomenon has not been advertised, hospitals have become reservoirs for resistant bacteria. A poignant need is therefore recognized for an alternative to conventional systemic antibiotics that will not incur the development of bacterial resistance.

2. SUMMARY OF THE INVENTION 2.1 Objects of the Invention

A primary object of the present invention is to provide a model for non-toxic antimicrobial agents that can be used systemically as an alterative to conventional systemic antibiotic, antiviral and antifungal therapies that do not incur the development of resistance by the target pathogens. Another object of the present invention is to provide a model for non-toxic antimicrobial agents that can be used systemically in gene therapy. Other auxiliary and ancillary objectives of the present invention may become apparent in a reading of the principles relating to said invention below and the detailed discussion of preferred embodiment following.

2.2 Principles Relating to the Present Invention

In achievement of the objects above it is suggested that cationic peptides efficacious in killing bacteria without incurring the development of bacterial resistance be utilized in a form that is non-toxic. Unexpectedly a branched cationic peptide composed of hystidine and lysine has more potent antimicrobial activity, and most unexpectedly no demonstrated toxicity, in comparison with a linear cationic peptide. A transport polymer comprised of a core and branched peptides possessing metabolizable peptide-bond linkages to a lysine core is specifically suggested for minimizing concerns with toxicity, improving antibacterial efficacy, and avoiding the development of bacterial resistance.

A branched peptide comprised of at least ten amino acid residues containing at least ten per cent histidine and at least ten per cent non-histidine amino acid residues is suggested. Cationic amino acids including lysine, arginine and ornithine are suggested for the non-histidine amino acids. Use of the transport polymer in conjunction with a pharmaceutical delivery component including a lipid, a microsphere, or another polymer, is also suggested. It is specifically suggested, in the case of a lipid, that a lamellar, uni or multi, liposome have the cationic peptide incorporated therein.

It is suggested that the peptide branches to the polymer be independently selected from the group of linear or branched polypeptides derived formulaically from at least one of the following seven sequences:

(1) K-H-K-H-K-H-K-G-K-H-K-H-K  SEQ ID NO: 1;

(2) K-H-K-H-K-H-K-G-K-H-K-H-K-H-K  SEQ ID NO: 2;

(3) K-H-K-H-K-H-K-H-K-G-K-H-K-H-K-H-K  SEQ ID NO: 3;

(4) K-H-K-H-K-H-K-H-K-G-K-H-K-H-K-G-K-H-K-H-K-K  SEQ ID NO: 4;

(5) K-H-K-H-K-H-K-H-K-H-K-H-K-H-K-H-K-  SEQ ID NO: 5;

(6) K-K-H-H-K-H-H-H-K-K-H-H-K-H-H-K-K  SEQ ID NO: 6;

(7) K-H-H-H-K-H-H-H-K-H-H-K-H-H-K  SEQ ID NO: 7;

wherein conventional single letter amino acid symbols are utilized with K=lysine, H=histidine, and G=glycine; and specifically including serial repetitions, reversals, and the following formulas:

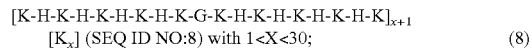

[K-H-K-H-K-H-K-H-K-G-K-H-K-H-K-H-K-H-K]$_{x+1}$
[K$_x$] (SEQ ID NO:8) with 1<X<30; (8)

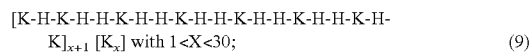

[K-H-K-H-H-K-H-H-K-H-H-K-H-H-K-H-H-K-H-
K]$_{x+1}$ [K$_x$] with 1<X<30; (9)

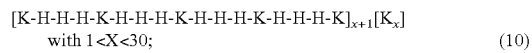

[K-H-H-H-K-H-H-H-K-H-H-H-K-H-H-H-K]$_{x+1}$[K$_x$]
with 1<X<30; (10)

wherein the initial amino acid within the brackets is the N-terminal amino acid of the polymer or a peptide branched thereto and the last amino acid within the brackets is the C-terminal end that is conjugated to the amino groups, α or ε, of the lysine core.

Peptide (8) may be equivalently expressed as [SEQ ID NO: 3]$_{x+1}$[K]$_x$. Peptide (9) may be equivalently expressed as [SEQ ID NO: 5]$_{x+1}$[K]$_x$. Peptide 10 may be equivalently expressed as [SEQ ID NO: 10]$_{x+1}$[K]$_x$. Where SEQ ID NO: 10 is K-H-H-H-K-H-H-H-K-H-H-H-K-H-H-H-K.

Administration of a pharmaceutical agent delivery composition including an active agent and a polymer in accordance with the formulae given above is also suggested. Bacteria, fungi, and viruses are encompassed as is intracellular infection. Both gram positive and negative bacteria are addressed. Viruses include enveloped containing viruses including retroviruses including HIV. Microbial organisms of both the animal and plant kingdoms are encompassed.

3. BRIEF DESCRIPTION OF THE DRAWING

FIG. 1 is a schematic of the structure of histidine-lysine branched copolymers used in antimicrobial and in vivo toxicity studies wherein the first three polymers are linear and polymers 4-8 are branches emanating from a core of lysine (K).

5. DETAILED DESCRIPTION OF PREFERRED EMBODIMENT

5.1 Definitions

The term 'amino acid' is inclusive of the twenty common amino acids as well as non-standard amino acids including D-amino acids and chemically or biologically produced derivatives of common amino acids.

A compound is 'associated with' a second compound if the two have formed a complex as a result of covalent or non-covalent interaction between the two.

'Copolymer' refers to a polymer containing two or more types of units regardless of the arrangement of units or molecular structure. A 'histidine copolymer' includes histidine as a unit type and comprises a 'transport polymer' in the present description.

The term 'peptide' includes linear, branched, and cyclic amino acid chains including at least two amino acid residues and the term 'polypeptide' connotes at least two joined peptides.

The term 'lipid' includes any chemical species having a hydrophobic or philic part enabling association with or incorporation into micelles or liposomes. Hydrophilicity typically is derived from the presence of phosphato, carboxylic, sulfato, amino, sulfhydryl, nitro and similar groups while hydrophobicity is typically conferred by cholesterol, its derivatives, or inclusion of groups including long chain saturated and unsaturated aliphatic hydrocarbons including substitution with at least one aromatic, cycloaliphatic, or heterocyclic group.

The term 'non-cationic lipid' refers to any of a number of lipid species existing in: an uncharged state, a neutral zwitterionic form, or an anionic form; at physiological pH including diacylphosphatidylcholine, diacylphoshatidylethanolamine, ceramide, sphingomyelin, cephalin, cardiolipin, cerbrosides, DOPE, and cholesterol.

The term 'cationic lipid' refers to any of a number of lipid species carrying a net positive charge including DODAC, DOTMA, DDAB, DOSPER, DOSPA, DOTAP, DC-Chol and DMRIE. A number of commercial preparations are available including: LIPOFECTIN® and LIPOFECTAMINE both from GIBCO/BRL, Grand Island, N.Y., USA; TRANSFECTAM® from Promega Corp., Madison, Wis., USA.

The term 'delivery component' connotes any stabilizing agent for cationic peptides in vivo or aids in the delivery of cationic peptides to an infectious organism including incorporation of cationic peptides into liposomes and ligands including PEG prolonging half life in blood.

An 'additive therapeutic infectious agent' is an adjunct to a cationic peptide delaying, preventing, or reducing the severity of infectious disease, i.e. reducing infection, including antibiotics and nucleic acids including RNA inhibitors effective against reiroviruses.

5.2 Pharmaceutical Agency

A branched cationic polypeptide polymer in accordance with the principles relating to the present invention comprised of histidine and other amino acid residues can be used alone or in association with a delivery component as a pharmaceutical agent preferably by incorporating the former into a stable complex with the latter and further preferably provided in a suitable pharmaceutically acceptable carrier. Said branched cationic polypeptide polymers can also be used alone as, or in association with, an additive therapeutic infections agent with or without an intracellular delivery component inclusive of pegylation, selected substitution of L-amino to D-amino acids, cell specific ligands, microspheres, lipids, and various lipid based substances including liposomes and micelles. A stabilizing compound covalently attached to either lipids or to cationic peptides can also be added. Polyethlene glycol is an example.

Preferred lipids form liposomes in a physiologically compatible environment including, for example, phosphatidylcholine, phosphatidylethanolamine, phosphatidylserine, dipalmitoylphosphatidylcholine, dioleoylphosphatidylcholine, distearoylphosphatidylcholine, dilinoleoylphosphatidylcholine. Lipids with a molarity of five to fifty per cent can be used with helper lipids such as cholesterol to increase stability in the bloodstream. And pegylated lipids in molar perentages of 0.05 to 0.5 can be used to prolong in vivo half life of the liposomes.

An additive therapeutic agent suitably comprises any agent that together with a branched cationic polypeptide polymer in accordance with the principles relating to the present invention demonstrates reduction in the infectious organism including, as example, antibiotics and nucleic acids administered separately from said branched cationic polypeptide polymer or in complex therewith by covalent or non-covalent bonding. Aminoglycosides, penicillin, cephalosporins, fluroquinolones, carbepenems, tetracylcines, and macrolides are examples of antibiotics that are considered useful for synergistic therapy with a branched cationic polypeptide polymer in accordance with the principles relating to the present invention. Plasmid based therapies, antisense, ribozymes, DNAzymes and RNA inhibitors provide examples of useful additive therapeutic infectious agents while RNAi in complex with said polymer is preferred.

5.3 Structure

A branched cationic polypeptide polymer in accordance with the principles relating to the present invention comprised of histidine and other amino acid residues preferably contains about twenty to three hundred said residues, more preferably thirty to a hundred, and most preferably thirty to seventy amino acid residues. The percentage constituency of histidine is preferably ten to ninety, more preferably twenty to eighty, and most preferably forty to seventy and are preferably interspersed uniformly into the transport polymer structure with at least one histidine residue in every segment of two to five amino acid residues. More preferably the distribution is at least one histidine residue in every segment of two to three and most preferably one in every two amino acid residues. Distribution of one to five histidine residues in every segment of two to five amino acid residues is suggested while one to four histidine residues in every segment of two to four amino acid residues is preferred. Non histidine residues are preferably distributed to achieve an average of one non-histidine residue in every segment of two to seven amino acid residues.

Preferred embodiment has the polymer branches bonded to a lysine core each comprised of one of the following formulas:

SEQ ID NO: 1;
(1) K-H-K-H-K-H-K-G-K-H-K-H-K

SEQ ID NO: 2;
(2) K-H-K-I-I-K-H-K-G-K-H-K-H-K-H-K

SEQ ID NO: 3;
(3) K-H-K-H-K-H-K-H-K-G-K-H-K-H-K-H-K-H-K

SEQ ID NO: 4;
(4) K-H-K-H-K-H-K-H-K-G-K-H-K-H-K-K-G-K-H-K-H-K-K

SEQ ID NO: 5;
(5) K-H-K-H-H-K-H-H-K-H-H-K-H-H-K-H-H-K-H-K-

-continued

SEQ ID NO: 6;
(6) K-K-H-H-H-K-H-H-H-K-K-H-H-H-K-H-H-H-K-K

SEQ ID NO: 7;
(7) K-H-H--H-K-H-H-H-K-H-H-H-K-H-H-K wherein conventional single letter amino acid symbols are utilized with K=lysine, H=histidine, and G=glycine; and specifically including serial repetitions and reversals.

A more preferred embodiment has the polymer branches bonded to a lysine core each comprised of one of and the following formulas:

[K-H-K-H-H-K-H-K-G-K-H-K-H-K-H-K-H-K]$_{x+1}$
[K$_x$] with 1<X<30;  (8)

[K-H-K-H-H-K-H-H-K-H-H-K-H-H-K-H-H-K-
H-K]$_{x+1}$[K$_x$] with 1<X<30;  (9)

[K-H-H-K-H-H-K-H-H-H-K-H-H-K-H-H-K]$_{x+1}$[K$_x$]
with 1<X<30;  (10)

wherein the initial amino acid within the brackets is the N-terminal amino acid of the polymer or a peptide branched thereto and the last amino acid within the brackets is the C-terminal end that is conjugated to the amino groups, α or ε, of the lysine core. In most preferred embodiment X ranges from three to five.

The backbone peptide or core of a branched cationic polypeptide polymer in accordance with the principles relating to the present invention can be constituted of any branching amino acid residue, preferably lysine, and between one and thirty peptide branches covalently attached to branching amino acid residues of the backbone peptide directly or through non-branching amino acid residues. The covalent bonding includes polypeptide, ester, and disulfide bonds.

Branching amino acids preferably possess a free amino side chain group: e.g. diaminobutyric acid, lysine, arginine, ornithine, diaminopropionic acid and citrulline; but can alternatively possess a free carboxyl side chain group: e.g. glutamic acid, aspartic acid, and homocitrulline.

A branched cationic polypeptide polymer in accordance with the principles relating to the present invention may also comprise a polypeptide-'synthetic monomer' copolymer wherein the transport polymer backbone comprises covalently linked segments of polypeptide and synthetic, preferably bio-compatible, monomer or polymer. Suitable monomers as well as methods for preparing a polypeptide-'synthetic monomer' copolymer are described in U.S. Pat. No. 4,511,478 for 'Polymerizable Compounds and Method for Preparing Synthetic Polymers that Integrally Contain Polypeptides' by Nowinski et al. incorporated by reference herein.

5.3.1 Methods of Manufacture

Polypeptides for use in manufacturing branched cationic polypeptide polymers in accordance with the principles relating to the present invention can be chemically synthesized and purified by techniques well known in the art. For example, by employing the N-α-9-fluorenylmethyloxycarbonyl or Fmoc solid phase polypeptide synthesis chemistry using a Rainin Symphony Multiplex Polypeptide Synthesizer.

Branched cationic polypeptide polymers in accordance with the principles relating to the present invention are made by including one or more amino acids within the amino acid sequence with a free side chain capable of forming a polypeptide bond with one or more amino acids, and thus capable of forming a 'branch', and reacting with a side chain to that locus. This can be done by any method for covalently linking any naturally occurring or synthetic amino acid to any naturally occurring or synthetic amino acid in a polypeptide chain which has a side chain group able to react with the amino or carboxyl group on the amino acids so as to become covalently attached to the polypeptide chain.

In particular, amino acids with a free amino side chain group including, as example, diaminobutyric acid, lysine, arginine, ornithine, diaminopropionic acid, and citrulline, can be incorporated into a polypeptide so that an amino acid can form a branch therewith by, for example, forming a polypeptide bond to the free amino side group from that residue. Alternatively, amino acids with a free carboxyl side chain group including, as example, glutamic acid, asparitic acid, and homocitrulline, can be incorporated into the polypeptide so that an amino acid can form a branch therewith, for example, by forming a polypeptide bond to the free carboxyl side group, from that residue. The amino acid forming the branch can be linked to a side chain group of an amino acid in the polypeptide chain by any type of covalent bond including polypeptide bonds, ester bonds and disulfide bonds.

The best known manner of preparation of branched cationic polypeptide polymers in accordance with the principles relating to the present invention follows.

For example, but not by way of limitation, branched polypeptides can be prepared as follows: (1) synthesize peptides on a Symphony multiple peptide synthesizer at a 0.025 mM scale using Fmoc (9-fluorenylmethyloxycarbonyl) chemistry, (2) remove Fmoc group (deprotection) with 20% piperidine/0.1M HOBt by incubating 3 times for 20 min; (3) following deprotection, wash resin 6 times for one min with DMF/DCM (1:1; primary solvent); (4) mix Fmoc-lysine (Dde) with HATU/DIEA in a 1:1:1.5 molar ratio; (5) mix activated amino acid with resin for 45 min at RT; (6) wash 3 times for 1 min with DMF/DCM; (7) cap any uncoupled free N-terminal amino groups on the resin using 50% acetic anhydride in DMF. Wash with capping reagent two times for 15 min; (8) wash 3 times for 1 min with the primary solvent; (9) repeat cycles of steps 2-8 to couple additional Fmoc-Lys (Dde) residues, dependent on the number of branches; (10) following the capping step after addition of the final Fmoc-Lys(Dde), remove Dde groups by incubation of the peptide resin in 2% hydrazine for 30 min; (11) wash peptide resin 6 times for 1 min with the primary solvent; (12) to add amino acids and to synthesize branches to the lysine core, remove Fmoc group (deprotection) by incubating 3 times for 20 min with 20% piperidine containing 0.1M HOBt; (13) following deprotection, wash the resin 6 times for one min with DMF/DCM (1:1; primary solvent); (14) catalyze amino acid coupling with HATU/DIEA as the activator. Mix Fmoc-Lysine (Boc), with HATU/DIEA in a 1:1:1.5 molar ratio; (15) mix activated amino acid with resin for 45 min at RT; wash 3 times for 1 min with the primary solvent; (16) cap any uncoupled free N-terminal amino groups on the resin using 50% acetic anhydride in DMF. Wash resin with 50% acetic anhydride in DMF two times for 15 min; (17) wash 3 times for 1 min with the primary solvent; (18) repeat steps a) through g) for each successive amino acid addition performed until the desired polymer is completed (a) remove Fmoc group (deprotection) by incubating 3 times for 20 min with 20% piperidine containing 0.1M HOBt. b) following deprotection, wash the resin 6 times for one mnin with DMF/DCM, c) Catalyze amino acid coupling with HATU/DIEA as the activator. Mix Fmoc-Lysine(Boc), with HATU/DIEA in a 1:1:1.5 molar ratio, d) Mix activated amino acid with resin for 45 min at RT, e) wash 3 times for 1 min with the primary solvent, f) cap any uncoupled free N-terminal amino groups on the resin using 50% acetic anhydride in DMF. Wash resin with 50% acetic anhydride in DMF two times for 15 min, and g) wash 3 times for 1 min with the primary solvent.) (19) cleave, purify, and analyze branched polymer, Branched polypeptides prepared by this method will have a substitution of lysine at the amino acid position, which is branched. Branched polypeptides containing amino acid analog substitution (e.g., diaminobutyric acid) can be prepared analogously to the procedure described above, using the t-Boc coupled form of the amino acid or amino acid analog.

5.4 Methods of Using the Pharmaceutical Agent

The invention comprises a method for delivering a pharmaceutical agent to an infectious agent. These agents may treat gram positive, gram negative, fungi, or viruses. Preferably, the compositions are administered to animals, including humans by injection. Injection may be systemic (by i.v. for systemic infections) or local (for example, injection to the site of a localized injection such a cellulitis or an abcess; aerosolized therapy for lung infections). In another preferred method of therapy, the pharmaceutical agent may be used as prophylactics prior to eye, cardiac, orthopedic, vascular, or pelvic surgery. The amount of polymer administered depends on a variety of factors known in the art, for example, the desired effect, subject state, etc., and can readily be determined by one skilled in the art.

Examples of gram positive bacteria treatable with the compositions and methods includes: *Staphylococcus aureus, Staphylococcus epidermidis, Staphylococcus saprophytics, Streptococcus pneumonia, Streptococcus enterococcus, Streptococcus pyogenes, Listeria monocytogenes Clostridium botulinum, Clostridium tetani, Clostridium difficile, Clostridium perfringens, Bacillus anthracis, Bacillus cereus, Bacillus thuringiensis, Bacillus mycoides, Bacillus subtilis, Micrococcus luteus, Mycobacterium tuberculosis, Peptococcus niger, Enterococcus faecalis, Enterococcus faecium, Erysipelothrix rhusiopathiae, Nocardia asteroides, Nocardia brasiliensis, Actinomyces actinomycetemcomitans, Actinomyces viscosus,* and *Actinomyces israeli.*

Examples of gram negative bacteria treatable with the compositions and methods includes: *Escherichia coli, Klebsiella pnuemoniae, Pseudomonas aeruginosa, Pseudomonas mallei, Pseudomonas melioidosis, Pseudomonas pseudomallei, Bacteroides fragilis, Bacteroides Thetaiolaomicron, Bacteroides melaninogeizicus, Bacteroides distasonis, Prevotella bivia, Prevotella disiens, Haemophilus influenzae, Haemophilus parainfluenzae, Haemophilus ducrey, Haemophilus aegypticus, Niesseria meningitidis, Niesseria gonorrhoeae, Legionella pneumophila, Salmonella enteritidi, Shigella dysenteriae, Proteus mirabilis, Proteus mirabilis, Enterobacter aerogenes, Enterobacter, cloacae, Enterobacter hafniae, Serratia marcecens, Citrobacter freundii, Yersinia pestis, Yersinia enterocolitica, Vibrio cholerae, Brucella abortus, Brucella melitensis, Brucella suis, Brucella canus, Bordetella pertussis, Bordetella parapertussis, Bordetella bronchiseptica, Campylobacter jejuni, Hellobacter pylori* and *Rickettsia rickettsii*

Examples of fungi treatable with the compositions and methods includes: *Candida Albicans, Cryptococcus neoformans, Aspergillus fumigatus, Aspergillus flavus, Aspergillus niger, Trichophyton rubrum, Trichophyton mentagrophytes, Microsporon lanosum, Microsporon canis, Microsporon audouini, Epidermophyton floccosum, Blastomyces dermatitidis, Coccidioides Immitis,* and *Histoplasma capsulatum.*

Examples of viruses treatable with the compositions and methods include viruses containing membrane envelopes including retroviruses (e.g., HIV).

6. EXAMPLES

The polymers in the Examples are based on histidine and lysine (or arginine) copolymers. Cationic amino acids are known to interact with the negatively charged membranes of bacteria or viruses (e.g., retroviruses). The data presented herein is consistent with the idea that both the cationic amino acid and histidine component of the copolymer and branching of the copolymer aid in the destruction of the bacteria.

6.1 Materials

Bacteria; A gram negative bacteria *E. coli* transformed with a kanamycin-resistant plasmid was used in these experiments and grown in LB media (Biofluids, Rockville, Md.).

Polymers: The biopolymer core facility at the University of Maryland synthesized the polymers on a Ranim Voyager synthesizer (PTI, Tuscon, Ariz.). The polymers were then purified on an HPLC (Beckman, Fullerton, Calif.) and analyzed with mass spectroscopy (Perseptive Biosystems, Foster City, Calif.) to verify the predicted molecular mass. Measurement of histidine copolymers with poly-L-lysine (Sigma Co., St. Louis, Mo.) used as a standard were done with 2,6-dinitro-4-trifluoromethylbenzenesulfonate (Pierce Co., Rockford, Ill.) as previously described. The following polymers were made: 1) R-H (19mer) [R-H-R-H-R-H-R-H-R-G-R-H-R-H-R-H-R-H-R] (SEQ ID NO: 8); 2) H-K (19mer) [K-H-K-H-K-H-K-H-K-G-K-H-K-H-K-H-K-H-K] (SEQ ID NO:3); 3) HK-R (19-mer) [R-H-K-H-K-H-K-H-K-G-K-H-K-H-K-H-K-H-K] (SEQ ID NO: 9); 4) H-K4b (79-mer) [K-H-K-H-K-H-K-H-K-G-K-H-K-H-K-H-K-H-K]$_4$K$_3$ (SEQ ID NO: 10); 5) H$^2$K2b (41-mer) [K-H-H-K-H-H-K-H-H-K-H-H-K-H-H-K-H-K]$_2$K (SEQ ID NO: 11); 6) H$^2$K4b (83-mer) [K-H-K-H-H-K-H-H-K-H-H-K-H-H-K-H-H-K-H-H-K-H-K]$_4$K$_3$ (SEQ ID NO: 12); H$^3$K4b (71-mer) [K-H-H-H-K-H-H-H-K-H-H-H-K-H-H-H-K]$_4$K$_3$ (SEQ ID NO: 13); 7) H$^3$ KN4b (71-mer) [K-H-H-H-N-H-H-H-K-H-H-H-K-H-H-H-K]$_4$K$_3$ (SEQ ID NO: 14). Note that 10 through 13 are branched polymers in which polymer is attached to the α and/or ε amino groups of the lysine residue and the central core of lysines are linked to one another by peptide bonds (FIG. 1).

6.2 In Vitro Bacteria Inhibition Studies:

For in vitro studies, several polymers were tested for their ability to inhibit gram negative bacteria. The linear polymers (HK, SEQ ID NO: 3; and RH, SEQ ID NO: 8) and the minimally branched HK (H$^2$K2b, SEQ ID NO: 11) showed only moderate reduction on bacteria growth. The highly branched polymers (H$^2$K4b, SEQ ID NO: 12; and H$^3$K4b, SEQ ID NO: 13) showed the most antimicrobial activity against a kanamycin-resistant bacteria. The histidine and lysine ratio and their sequence order have an important role in the-polymers' effects. The following conclusions can be made:

1) the polymer with greatest number of lysines (e.g., HK4b, SEQ ID NO: 10) did not show the highest antimicrobial activity. This indicates that there is another factor besides the interaction of the positively charged amino acids with the negatively charged membranes of the bacteria.

2) the polymer, H$^3$KN4b (SEQ ID NO: 14) with the most histidines and the highest histidine:lysine ratio showed moderate antimicrobial activity when compared to H$^2$K4b (SEQ ID NO: 12) and H$^3$K4b (SEQ ID NO: 13). Since it is likely that H$^3$KN4b has the greatest ability to chelate key transitional elements, chelation of key elements in LB media, separate from the polymer's role of binding to the bacteria membrane, is unlikely to have a major role in the inhibition of bacteria.

3) The sequence order of lysine and histidine in the branched polymer has a major role in the inhibition of bacteria.

Altering these sequences affects the antibacterial activity of the bacteria. Sufficient cationic amino acids are critical for binding whereas the exact function of histidine is unclear. Data supports that cationic amino acids need to be evenly distributed in branches, particularly at N-terminal ends. Too many cationic amino acids in the polymer, however, reduce antibacterial activity.

4) Histidine may have a role in the interruption of iron transport systems and/or it may enhance the hydrophobic interactions of the polymer with the bacteria membrane. Regardless of the antibacterial mechanism of histidine within the polymer, lowering the histidine: lysine ratio significantly reduces antibacterial activity.

5) Linear Polymers inhibit bacteria significantly, less than branched polymers.

TABLE 1

MIC of HK and RK Polymere

| | Polymers | MIC |
|---|---|---|
| 1. | linear HK | >300 µg/ml |
| 2. | linear RH | >300 µg/ml |
| 3. | H$^2$K2b (2 branches) | >300 µg/ml |
| 4. | HK4b (4 branches) | 198 µg/ml |
| 5. | H$^2$K4b (4 branches) | 58 µg/ml |
| 6. | H$^2$K4b (4 branches) | 110 µg/ml |
| 7. | H$^3$KN4b (4 branches) | 250 µg/ml |

Turbidity of bacteria (O.D.-600 nm) measured after incubation for 12 h at 37° C. with various polymers and compared to bacterial-containing medium without polymer. Several concentrations of polymers (300, 150, 100, 50 and 25 µg) were added to the 1-ml of LB broth containing bacteria. Polymer numbers 4 to 7 have an increasing higher content of histidine compared to lysine, but the same degree of branching. The MIC is the concentration of the inhibitor in the medium in which bacteria growth is completely inhibited. Experiment has been repeated 3 times. HK4b, the polymer with the most lysines, does not have the most activity in reducing bacteria growth. Also, H$^3$KN4b, the polymer with most histidines and the highest histidine:lysine ratio, is not the most active.

6.3 In vitro Toxicity

In vitro toxicity of these polymers was then examined on a malignant cell line (MDA-MB-435). In this cell line, the most effective antimicrobial HK polymers showed the least toxicity (as measured by cell number) (see Table 2). Unexpectantly, the linear HK polymer was significantly more toxic to MDA-MB-435 cells compared to its branched counterparts. In contrast, H$^3$K4b had no observed toxicity in these in vitro studies.

TABLE 2

Reduction In Cell Number After Incubation with Polymers

| Polymer | 150 µg/ml | 100 µl/ml | 50 µg/ml |
|---|---|---|---|
| linear HK | 65% | 68% | 41% |
| H$^2$K4b | 22% | 12% | 5% |
| H$^3$K4b | 0% | 0% | 0% |

Incubation of 3 polymers at 3 concentrations (150, 100, 50 µg/ml) for 6 h in DMEM/10% serum containing MDA-MB-435 cells. 24 h later, cell numbers were counted for each polymer condition and compared to untreated cells. This experiment was done twice and each condition has been done in duplicate per experiment. Similar results were observed when polymers were incubated with MDA-MB-435 cells in the presence of DMEM without serum.

6.4 In Vivo Studies:

One of the major limitations of cationic peptides is their potenitial toxicity when administered systemically. As a result, we tested the acute toxicity of these polymers after injecting them IV. Interestingly, the polymers (branched polymers) that were the most active against bacteria in vitro showed no evidence of toxicity in vivo (Table 3). Furthermore, mice who received three-600 µg dosages of the H$^3$K4b polymer (each separated by 4 h) showed no evidence of toxicity (e.g., no decreased activity or paleness). Conversely, linear polymers that had minimal to moderate antibacterial properties had the greatest in vivo toxicity. The most toxic of the linear polymers was the linear polymer, HR. Even if one arginine adjacent to the histidine residue replaces the amino terminal lysine in the HK polymer (e.g., HK-R), the polymer was still very toxic when administered intravenously. The in vivo toxicity of linear HK polymers from most to least is as follows: HR>HK-R>>HK. For mice who died from polymers (HR, HK-R, and HK) at higher dosages, histology of major organs showed no evidence of pathology. There were parallels between in vitro and in vivo toxicity studies (Tables 2 and 3). That is, linear polymers demonstrated the most toxic in these studies. The data is consistent with linear polymers interacting and inhibiting ionic channels of the cardiovascular system (similar to neurotoxins). Intravenous injection of linear polymers with arginine or lysines adjacent (or near) to histidines should be avoided. In contrast, mice who received large dosages of the branched HK polymers injected i.v. showed no untoward effects.

TABLE 3

Acute In Vivo Toxicity

| Polymers | 600 µg | 300 µg | 150 µg | 75 µg |
|---|---|---|---|---|
| HR | 0/2 | 0/2 | 2/2 (+++, +) | 2/2 (+) |
| HK-R | 0/2 | 0/2 | 2/2 (+, +) | 2/2 |
| HK | 0/2 | 2/2 (+++, +++) | 2/2 (++, +) | 2/2 |
| HK4b | 2/2 | 2/2 | 2/2 | 2/2 |
| H$^2$K4b | 2/2 | 2/2 | 2/2 | 2/2 |
| H$^3$K4b | 2/2 | 2/2 | 2/2 | 2/2 |

Numerator denotes the number of mice who survive treatment, and denominator denotes number of mice in each treatment group. Each mouse who survived injection but had side effects was defined by the following scale:
+++, inactive for at least 1 min, extreme pallor,
++, moderate reduction in activity for at least 1 min;
+, moderate reduction in activity in for less than 1 min.

Many of these polymers were initially developed as gene therapy carriers of nucleic acids. Although the nucleic acids mitigated the toxic reactions of the above polymers when administered i.v., the polymers in complex with nucleic acids showed parallels in toxicity when the polymers alone were administered i.v.

6. REFERENCES

Throughout this specification various patent and non-patent references have been mentioned. The entire disclosure of each such reference is incorporated herein by reference, as is the entire disclosure of each of the following references, to the extent relevant to making and using the intervention as claimed:

Bechinger, B., Kinder R., Helmle, M., Vogt, T. C., Harzer, U. and Schinzel, S. (1999). Peptide structural analysis by solid-state NMR spectroscopy. *Biopolymers* 51, 174-90.

Bellm, L., Lehrer, R. I. and Ganz, T. (2000). Protegrins: new antibiotics of mammalian origin. *Expert Opin. Investig Drugs* 9, 1731-42.

Blanc, E., Fremont, V., Sizun, P., Meunier, S., Van Rietschoten, J., Thevand, A., Bernassau, J. M. and Darbon, H.

(1996). Solution structure of P01, a natural scorpion peptide structurally analogous to scorpion toxins specific for apamin-sensitive potassium channel. *Proteins* 24, 359-69.

Bontems, F., Roumestand, C., Gilquin, B., Menez, A. and Toma, F. (1991). Refined structure of charybdotoxin; common motifs in scorpion toxins and insect defensins. *Science* 254, 1521-3.

Chen, Q. R., Zhang, L., Stass, S. A. and Mixson, A. J. (2001). Branched co-polymers of histidine and lysine are efficient carriers of plasmids. *Nucleic Acids Res.* 29, 1334-1340.

Cruz, L. J., Johnson, D. S. and Olivera, B. M. (1987). Characterization of the omega-conotoxin target. Evidence for tissue-specific heterogencity in calcium channel types. *Biochemistry* 26, 820-4.

Dathe, M. and Wieprecht, T. (1999). Structural features of helical antimicrobial peptides: their potential to modulate activity on model membranes and biological cells. *Biochim Biophys Acta* 1462, 71-87.

Epand, R. M. and Vogel, H. J. (1999). Diversity of antimicrobial peptides and their mechanisms of action. *Biochim Biophys Acta* 1462, 11-28.

Giacometti, A., Cirioni, O., Ghiselli, R., Viticchi, C., Mocchegianzi, F., Riva, A., Saba, V. and Scalise, G. (2001). Effect of mono-dose intraperitoneal ecropins in experimental septic shock. *Crit Care Med* 29, 1666-9.

Gilles, N., Krimm, I., Boust, F., Froy, O., Gurevitz, M., Lancelin, J. M. and Gordon, D. (2000). Structural implications on the interaction of scorpion alpha-like toxins with the sodium channel receptor site inferred from toxin iodination and pH-dependent binding. *J Neurochem* 75, 1735-45.

Hancock, R. E. (1997). Peptide antibiotics. *Lancet* 349, 418-22.

Hancock, R. E. (1999). Host defense (cationic) peptides: what is their future clinical potential? *Drugs* 57, 469-73.

Hancock, R. E. and Lehrer, R. (1998). Cationic peptides: a new source of antibiotics. *Trends Biotechnol* 16, 82-8.

Harder, J., Bartels, J., Christophers, E. and Schroder, I. M. (2001). Isolation and characterization of human beta-defensin-3, a novel human inducible peptide antibiotic. *J Biol Chem* 276, 5707-13.

Hoover, D. M., Chertov, O. and Lubkowski, J. (2001). The structure of human beta-defensin-1: new insights into structural properties of beta-defensins. *J Biol Chem* 276, 39021-6.

Hughes, A. L. (1999). Evolutionary diversification of the mammalian defensins. *Cell Mol Life Sci* 56, 94-103.

Jia, H. P., Mills, J. N., Barahmand-Pour, F., Nishimura, D., Mallampali, R. K., Wang, G., Wiles, K., Tack, B. F., Bevins, C. L. and McCray, P. B., Jr. (1999). Molecular cloning and characterization of rat genes encoding homologues of human beta-defensins. *Infect Immun* 67, 4827-33.

Kourie, J. I. and Shorthouse, A. A. (2000). Properties of cytotoxic peptide-formed ion channels. *Am J Physiol Cell Physiol* 278, C1063-87.

La Rocca, P., Biggin, P. C., Tieleman, D. P. and Sansom, M. S. (1999). Simulation studies of the interaction of antimicrobial peptides and lipid bilayers. *Biochim Biophys Acta* 1462, 185-200.

Lehrer, R. I. and Ganz, T. (1996). Endogenous vertebrate antibiotics. Defensins, protegins, and other cysteine-rich antimicrobial peptides. *Ann N Y Acad Sci* 797, 228-39.

Mallow, E. B., Harris, A., Salzman, N., Russell, J. P., DeBerardinis, R. J., Ruchelli, E. and Bevins, C. L. (1996). Human enteric defensins. Gene structure and developmental expression. *J Biol Chem* 271, 4038-45.

Martin, M. F. and Rochat, H. (1984). Purification of thirteen toxins active on mice from the venom of the North African scorpion *Buthus occitamus tunetanus*. *Toxicon* 22, 279-91.

Mosca, D. A., Hurst, M. A., So, W., Viajar, B. S., Fujii, C. A. and Falla, T. J. (2000). IB-367, a protegrin peptide with in vitro and in vivo activities against the microflora associated with oral mucositis. *Antimicrob Agents Chemother* 44, 1803-8.

Oppenheim, F. G., Xu, T., McMillian, F. M., Levitz, S. M., Diamond, R. D., Offner, G. D. and Troxler, R. F. (1988b). Histatins, a novel family of histidine-rich proteins in human parotid secretion. Isolation, characterization, primary structure, and fungistatic effects on *Candida albicans*. *J Biol Chem* 263, 7472-7.

Oppenheim, F. G., Xu, T., McMillian, F. M., Levitz, S. M., Diamond, R. D., Offner, G. D. and Troxler, R. F. (1988a). Histatins, a novel family of histidine-rich proteins in human perotid secretion. Isolation, characterization, primary structure, and fungistatic effects on *Candida albicans*. *J Biol Chem* 263, 7472-7.

Oren, Z., Lerman, J. C., Gudmundsson, G. H., Agerberth, B. and Shai, Y. (1999). Structure and organization of the human antimicrobial peptide LL-37 in phospholipid membranes: relevance to the molecular basis for its non-cell-selective activity. *Biochem J* 341, 501-13.

Oren, Z., Ramesh, J. Avrahami, D., Suryaprakash, N., Shai, Y. and Jelinek, R. (2002). Structures and mode of membrane interaction of a short alpha helical lyric peptide and its diastereomer determined by NMR, FTIR, and fluorescence spectroscopy. *Eur J Biochem* 269, 3869-80.

Oren, Z. and Shai, Y. (1998). Mode of action of linear amphipathic alpha-helical antimicrobial peptides. *Biopolymers* 47, 451-63.

Otvos, L., Jr. (2000). Antibacterial peptides isolated from insects. *J Pept Sci* 6, 497-511. Otvos, L., Jr., Bokonyi, K., Varga, I., Otvos, B. I., Hoffmann, R., Ertl, H. C., Wade, J. D., McManus, A. M., Craik, D. J. and Bulet, P. (2000). Insect peptides with improved protease-resistance protect mice against bacterial infection. *Protein Sci* 9, 742-9.

Peschel, A. and Collins, L. V. (2001). Staphylococcal resistance to antimicrobial peptides of mammalian and bacterial origin. *Peptides* 22, 1651-9.

Sabatini, L. M. and Azen, E. A. (1989). Histatins, a family of salivary histidine-rich proteins, are encoded by at least two loci (HIS1 and HIS2). *Biochem Biophys Res Commun* 160, 495-502.

Sitaram, N. and Nagaraj, R. (1999). Interaction of antimicrobial peptides with biological and model membranes; structural and charge requirements for activity. *Biochim Biophys Acta* 1462, 29-54.

Thomas, N. J., Carcillo, J. A., Doughty, L. A., Sasser, H. and Heine, R. P. (2002). Plasma concentrations of defensins and lactoferrin in children with severe sepsis. *Pediatr Infect Dis J* 21, 34-8.

Tsai, H. and Bobek, L. A. (1998). Human salivary histantins: promising anti-fungal therapeutic agents. *Crit Rev Oral Biol Med* 9, 480-97.

Vogel, H. J., Schibli, D. J., Jing, W., Lohmeier-Vogel, E. M., Epand, R. F. and Epand, R. M. (2002). Towards a structure-function analysis of bovine lactoferricin and related tryptophan- and arginine-containing peptides. *Biochem Cell Biol* 80, 49-63.

Yang, D., Biragyn, A., Kwak, L. W. and Oppenheim, J. J. (2002). Mammalian defensins in immunity: more than just microbicidal. *Trends Immunol* 23, 291-6.

What is claimed is:

1. A method for treating bacteria, fungal, or viral infections comprising administering a branched polymer with a backbone of 1 or more amino acid residues and at least one branch with at least 10 amino acid residues, wherein at least 38% of the amino acid residues are histidine and at least 10% of the amino acid residues are non-histidine.

2. The method of claim 1, wherein at least 50% of the amino acids of said branched polymer are histidines.

3. The method of claim 1, wherein at least 70% of the amino acids of said branched polymer are histidines.

4. The method of claim 1, wherein at least 20% of non-histidine amino acid residues are amino acids which carry a positive charge at physiological pH.

5. The method of claim 4, wherein the positively charged non-histidine amino acid residues are lysines.

6. The method of claim 1, wherein said branched polymer comprises a subsegment of amino acid residues selected from the group consisting of:
K-H-K-H-K-H-K-G-K-H-K-H-K (SEQ ID NO: 1),
K-H-K-H-K-H-K-G-K-H-K-H-K-H-K (SEQ ID NO: 2),
K-H-K-H-K-H-K-H-K-G-K-H-K-H-K-H-K-H-K (SEQ ID NO: 3),
K-H-K-H-K-H-K-H-K-G-K-H-K-H-K-H-K-H-K-G-K-H-K-H-K-H-K-H-K (SEQ ID NO: 4),
K-H-K-H-H-K-H-H-K-H-H-K-H-H-K-H-H-K-H-K (SEQ ID NO: 5),
K-K-H-H-H-K-H-H-H-K-K-H-H-H-K-H-H-H-K-K (SEQ ID NO: 6),
K-H-H-H-K-H-H-H-K-H-H-H-K-H-H-H-K (SEQ ID NO: 7),
end-to-end repeats of one or more of the above sequences, and
the reverse of any of the above sequences.

7. The method of claim 6, wherein said branched polymer is selected from the group consisting of:
[K-H-K-H-H-K-H-H-K-H-H-K-H-H-K-H-H-K-H-K]$_4$ K$_3$ (SEQ ID NO: 12),
[K-H-H-H-K-H-H-H-K-H-H-H-K-H-H-H-K]$_4$ K$_3$ (SEQ ID NO: 13).

8. The method of claim 1, comprising administering the branched polymer with at least one delivery component.

9. The method of claim 8, wherein the delivery component comprises a lipid.

10. The method of claim 1, wherein the infection is septic shock.

11. The method of claim 1, further comprising administering an additive therapeutic infectious agent selected from the group consisting of antibiotics and/or nucleic acids; and optionally a delivery component.

12. The method of claim 11, wherein the additive therapeutic infectious agent comprises RNAi nucleic acid that targets viral infections.

13. The method of claim 1, wherein the infection is local or systemic.

14. The method of claim 1, wherein the infection is a fungal infection.

15. The method of claim 1, wherein the backbone of the branched polymer consists entirely of lysine residues.

* * * * *

SEQUENCE LISTING

<160> NUMBER OF SEQ ID NOS: 11

<210> SEQ ID NO 1
<211> LENGTH: 13
<212> TYPE: PRT
<213> ORGANISM: Artificial
<220> FEATURE:
<223> OTHER INFORMATION: Cationic peptide

<400> SEQUENCE: 1

Lys His Lys His Lys His Lys Gly Lys His Lys His Lys
1               5                   10

<210> SEQ ID NO 2
<211> LENGTH: 17
<212> TYPE: PRT
<213> ORGANISM: Artificial
<220> FEATURE:
<223> OTHER INFORMATION: Cationic peptide

<400> SEQUENCE: 2

Lys His Lys His Lys His Lys Gly Lys His Lys His Lys His Lys His
1               5                   10                  15

Lys

<210> SEQ ID NO 3
<211> LENGTH: 19
<212> TYPE: PRT
<213> ORGANISM: Artificial
<220> FEATURE:
<223> OTHER INFORMATION: Cationic peptide

<400> SEQUENCE: 3

Lys His Lys His Lys His Lys His Lys Gly Lys His Lys His Lys His
1               5                   10                  15

Lys His Lys

<210> SEQ ID NO 4
<211> LENGTH: 23
<212> TYPE: PRT
<213> ORGANISM: Artificial
<220> FEATURE:
<223> OTHER INFORMATION: Cationic peptide

<400> SEQUENCE: 4

Lys His Lys His Lys His Lys His Gly Lys His Lys His Lys Lys
1               5                   10                  15

Gly Lys His Lys His Lys Lys
            20

<210> SEQ ID NO 5
<211> LENGTH: 20
<212> TYPE: PRT
<213> ORGANISM: Artificial
<220> FEATURE:
<223> OTHER INFORMATION: Cationic peptide

<400> SEQUENCE: 5

Lys His Lys His His Lys His Lys His Lys His Lys His Lys His
1               5                   10                  15

His Lys His Lys
        20

```
<210> SEQ ID NO 6
<211> LENGTH: 20
<212> TYPE: PRT
<213> ORGANISM: Artificial
<220> FEATURE:
<223> OTHER INFORMATION: Cationic peptide

<400> SEQUENCE: 6

Lys Lys His His His Lys His His His Lys Lys His His His Lys His
1               5                   10                  15

His His Lys Lys
            20

<210> SEQ ID NO 7
<211> LENGTH: 18
<212> TYPE: PRT
<213> ORGANISM: Artificial
<220> FEATURE:
<223> OTHER INFORMATION: Cationic peptide

<400> SEQUENCE: 7

Lys His His His His Lys His His His Lys His His His Lys His His
1               5                   10                  15

His Lys

<210> SEQ ID NO 8
<211> LENGTH: 19
<212> TYPE: PRT
<213> ORGANISM: Artificial
<220> FEATURE:
<223> OTHER INFORMATION: Charged peptide

<400> SEQUENCE: 8

Arg His Arg His Arg His Arg His Arg Gly Arg His Arg His Arg His
1               5                   10                  15

Arg His Arg

<210> SEQ ID NO 9
<211> LENGTH: 19
<212> TYPE: PRT
<213> ORGANISM: Artificial
<220> FEATURE:
<223> OTHER INFORMATION: Charged peptide

<400> SEQUENCE: 9

Arg His Lys His Lys His Lys His Lys Gly Lys His Lys His Lys His
1               5                   10                  15

Lys His Lys

<210> SEQ ID NO 10
<211> LENGTH: 17
<212> TYPE: PRT
<213> ORGANISM: Artificial
<220> FEATURE:
<223> OTHER INFORMATION: Charged peptide

<400> SEQUENCE: 10

Lys His His His Lys His His His Lys His His His Lys His His His
1               5                   10                  15

Lys

<210> SEQ ID NO 11
<211> LENGTH: 17
```

```
<212> TYPE: PRT
<213> ORGANISM: Artificial
<220> FEATURE:
<223> OTHER INFORMATION: Charged peptide

<400> SEQUENCE: 11

Lys His His His Asn His His Lys His His Lys His His
1               5                   10              15

Lys
```